United States Patent [19]

Masaaki et al.

[11] Patent Number: 4,933,566

[45] Date of Patent: Jun. 12, 1990

[54] METHOD OF DETECTING TAPE DEFECTS

[75] Inventors: Sakaguchi Masaaki; Kazuo Kubota, both of Kanagawa, Japan

[73] Assignee: Fuji Photo Film Co., Ltd., Kanagawa, Japan

[21] Appl. No.: 279,394

[22] Filed: Nov. 30, 1988

[30] Foreign Application Priority Data

Nov. 30, 1987 [JP] Japan ................... 62-303038

[51] Int. Cl.$^5$ .......................................... G01N 21/88
[52] U.S. Cl. ..................................... 250/563; 356/431
[58] Field of Search ..................... 250/562, 563, 572; 356/430, 431

[56] References Cited

U.S. PATENT DOCUMENTS 3,843,890 10/1974 Anthony ............................ 250/572
3,988,530 10/1976 Ikegami ............................. 250/562
4,118,127 10/1978 Klein .................................. 356/431

Primary Examiner—David C. Nelms
Assistant Examiner—Sherrie Hsia
Attorney, Agent, or Firm—Sughrue, Mion, Zinn, MacPeak & Seas

[57] ABSTRACT

A method of detecting tape defects according to a light amount signal obtained from the surface of a tape by scanning the width of the tape surface with a light beam is disclosed. The light beam is caused to scan beyond the tape edges. The light amount signal is differentiated to obtain a light amount differential signal. A tape defect in the vicinity of the tape edge is detected if the light amount differential signal has a level different from a predetermined reference level or if the point in time when a change in the level of the light amount differential signal is different from a predetermined point in time.

13 Claims, 4 Drawing Sheets

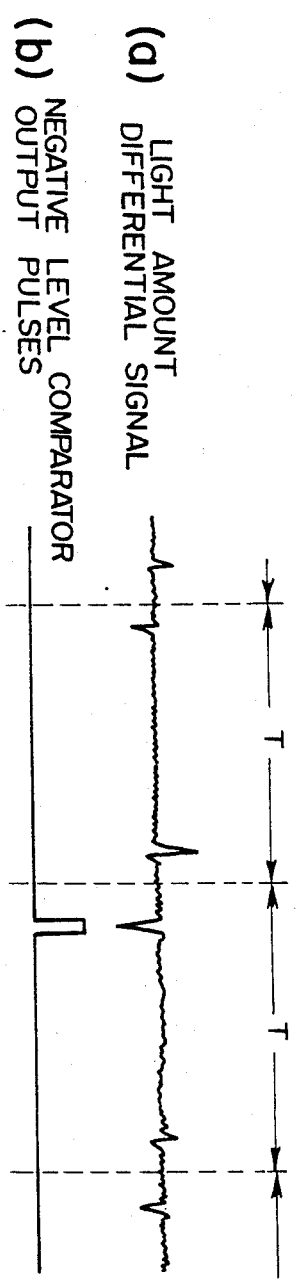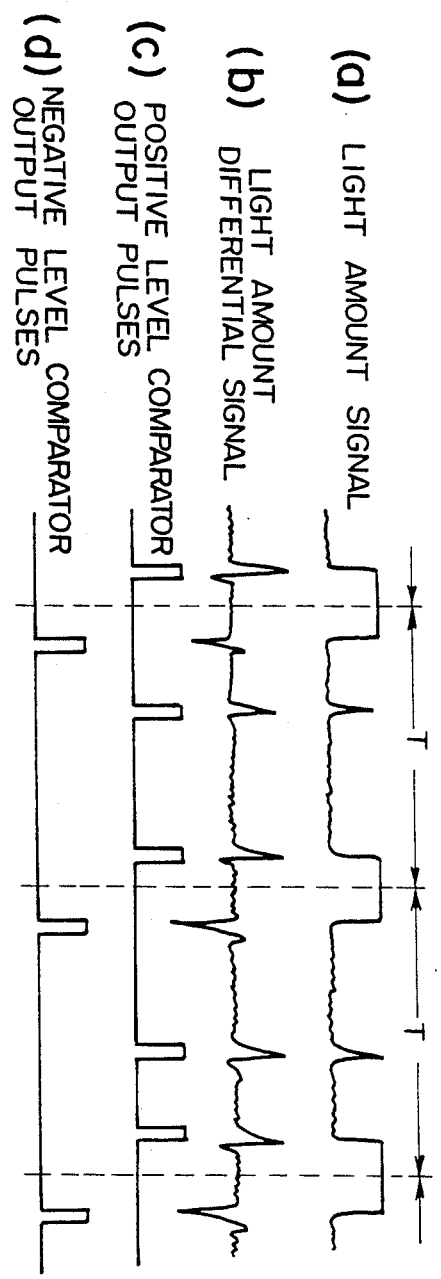
FIG. 3
FIG. 4

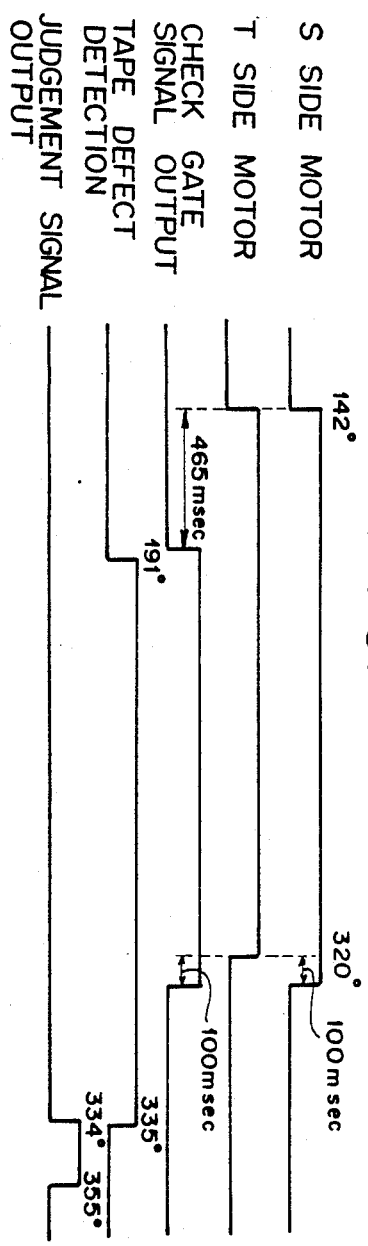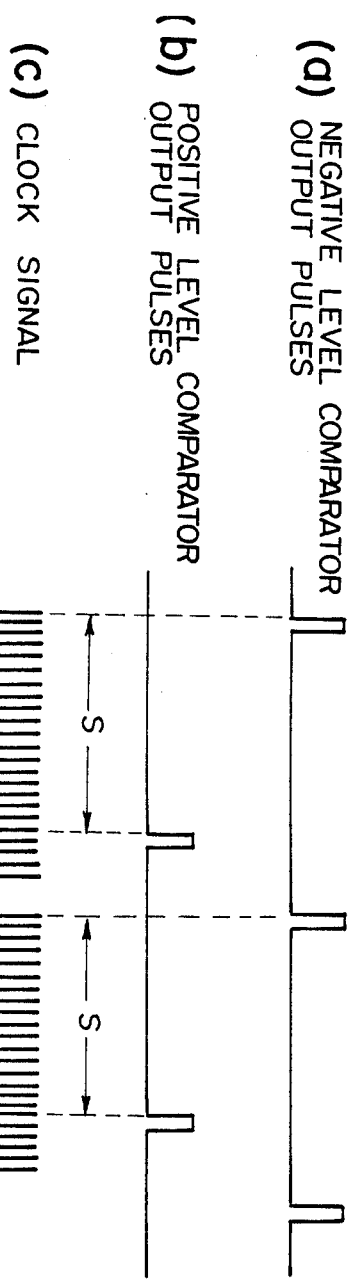
FIG. 5
FIG. 6

METHOD OF DETECTING TAPE DEFECTS

BACKGROUND OF THE INVENTION

1. Field of the Invention

This invention relates to a method of automatically detecting tape defects on a magnetic tape or like tape having a fixed width, e.g., a video tape or an audio tape, and more particularly to a tape defect detection method for detecting tape defects according to light amount data obtained from the tape surface by scanning the width of the tape with a light beam.

2. Description of the Prior Art

Tape defects in audio tapes and other similar magnetic tapes, which are due to scars or scratches, deformation, or attachment of foreign particles, lead to deterioration of the tape quality. Therefore, tape defect detection is performed in the process of tape manufacture to sort out and stop shipment of tapes with tape defects.

A method of detecting tape defects is known in which a tape running in its longitudinal direction is scanned across its width with a light beam, and light reflected from the tape surface is detected. Tape defects are checked by using light amount data available from the detected reflected light.

With this prior art technique, it is possible to satisfactorily detect tape defects present in a middle portion of the width of the tape. However, it is difficult to satisfactorily detect tape defects present in places near the tape edges (hereinafter called edge portions), when scanning the width of the tape. This is due to the fact that an edge signal, produced by a great change in the amount of light reflected from the tape at the edge thereof, is difficult to distinguish from a tape defect signal. Also, overshoots occurring when the edge signal rises and falls make accurate measurement of these tape defects difficult.

Heretofore, usually only a middle portion of the width of the tape was used as a recording area, so that tape defects present near the tape edge presented no serious problems.

However, recent demands for size reduction and an increase in the density of the information stored on the recording media require the use of even tape edge portions for recording. To meet these demands, the development of a tape defect detection method, which can accurately detect tape defects present in tape edge portions, is desirable.

SUMMARY OF THE INVENTION

The purpose of the present invention is to satisfy the above demands, and its object is to provide a tape defect detection method, which can accurately detect tape defects present in edge portions of a tape.

To attain the above object of the invention, there is provided a method of detecting tape defects with a light amount signal, which is obtained by scanning the width of a tape surface with a light beam, the light beam being caused to continue scanning beyond the tape edges. When the light beam crosses a tape edge, the light amount signal is differentiated to obtain an edge differential signal, and a tape defect in the vicinity of the tape edge is detected if the edge differential signal has a level different from a predetermined reference level.

Also, to attain the above object of the invention there is provided a method of detecting tape defects with a light amount signal, which is obtained by scanning the width of a tape surface with a light beam, the light beam being caused to continue scanning beyond the tape edges and in which tape defect detection method a point of change in the level of a light amount signal obtained when the light beam crosses a tape edge is referenced to a predetermined point in time, and a tape defect is detected in the vicinity of the tape edge if the detection of a point of change in the level of the light amount signal is different from the predetermined reference point in time.

When the light beam crosses a tape edge the amount of light incident on the light-receiving means changes greatly, thus producing a light amount signal, which has a series of rectangular pulses in its waveform. This part of the light amount signal, which changes rapidly from one level to another when the light beam crosses an edge, is referred to by the term "a light amount signal obtained when the light beam crosses a tape edge".

In the first-mentioned tape defect detection method according to the invention, the light amount signal, which exhibits a waveform having rectangular pulses, is differentiated to obtain an edge differential signal, when the light beam crosses the tape edge, and a tape defect is detected in the vicinity of the tape edge if the edge differential signal has a level different from the predetermined reference level. If the tape edge has a tape defect such as a gentle bend or a defect such as attached foreign particles, the pulsed waveform of the light amount signal will be different from the shape of the signal when no tape defect exists. It may look more like a stepped waveform, and consequently the value of the differential of the edge signal has a level different from the reference level, which reference level results when no tape defects exist, as confirmed from experimental results. The reference signal level which determines when tape defects are detected is based on experimental results. It is thus possible to accurately detect tape defects in the vicinity of the tape edges, which could not hitherto be detected from mere observation of the light amount signal level. Thus this method can greatly contribute to the rejection of tapes with tape defects and the improvement of the quality of tapes shipped out of the factory.

In the second-mentioned tape defect detection method according to the invention, a point of change in the level of the light amount signal, which light amount signal exhibits a pulsed waveform when the light beam crosses a tape edge, is detected, and if the timing of the detected change point in the level of the light amount signal is different from the predetermined reference timing, then the presence of a tape defect is indicated. When the tape edge is damaged or when the width of the tape is larger than normal due to defective tape cutting, the shape of the light amount signal is different from that in which tape defects are absent, as confirmed from experimental results. Whether or not a defect exists is based on experimental result. It is thus possible to accurately detect a tape defect such as a sharp bend or the like along the edge of a tape, which could not hitherto be detected from mere observation of the light amount signal. The method thus can greatly contribute to the rejection of tapes with tape defects and improvement in the quality of tapes shipped out of the factory.

BRIEF DESCRIPTION OF THE DRAWINGS

FIGS. 3, 4 and 5, which include FIGS. 3(a), 3(b), 3(c) and 3(d), FIGS. 4(a) and 4(b), and FIGS. 5(a), 5(b) and 5(c), respectively, are timing charts showing signal timings, which signals are provided by various parts of the circuit of the system shown in FIG. 1;

FIG. 6 gives a sample of a timing chart for explaining the operation of various parts of the system shown in FIG. 1.

DETAILED DESCRIPTION OF THE PREFERRED EMBODIMENTS

Now, an embodiment of the invention will be described with reference to the drawings.

Figure 1:
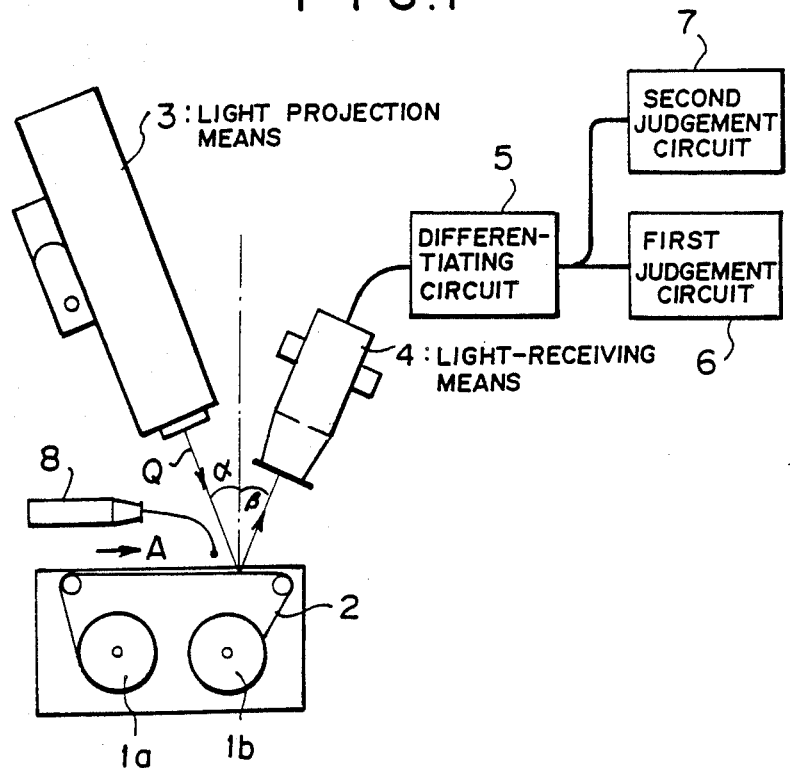
FIG. 1 is a schematic representation of a tape defect detector for carrying out an embodiment of the method according to the present invention.

FIG. 1 is a schematic representation of a tape defect detector for carrying out one embodiment of the method according to the invention. The detector comprises light projection means 3 for projecting a light beam Q onto a magnetic tape 2 driven at a constant speed in the direction of arrow A between reels 1a and 1b for luster-scanning the tape, light-receiving means 4 for receiving a light beam, which has been projected from light projection means 3 and reflected by the surface of the magnetic tape 2. The detector also comprises a light-receiving means 4 for generating a light amount signal, corresponding to the level of the light which is received, and a differentiating circuit 5 for differentiating the light amount signal to obtain a light amount differential signal, a first detection circuit 6 for comparing the level of the light amount differential signal to a predetermined reference level and providing a first detection signal representing the result of the comparison and a second detection circuit 7 for comparing the light amount differential signal to a predetermined reference timing and providing a second detection signal representing the result of the second comparison. A fiber sensor 8 is provided near the position at which the light beam is incident on the magnetic tape. The sensor 8 helps to set a check timing by detecting a tape juncture. The light incidence surface of the fiber sensor 8 is located at a position 20 mm, for instance, from the surface of the tape 2.

Figure 2:
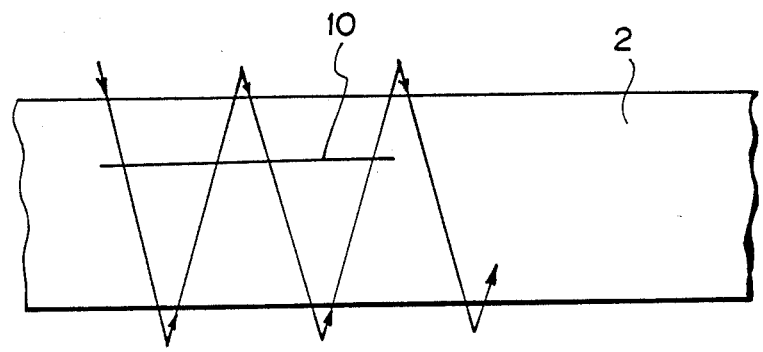
FIG. 2 is a schematic view for explaining the scanning of a tape with a light beam from a light projectin means shown in FIG. 1.

The light beam Q from the light projection means 3 scans the tape width a fixed number of times per second. Since the tape 2 is driven at a constant speed, the light beam luster scans the surface of the tape 2 as shown in FIG. 2. The angle α of incidence of the light beam Q on the magnetic tape 2 and angle β of reflection is set to, for instance, 22.5°. The reels 1a and 1b may be driven by using a small motor such as that used in an ordinary cassette deck.

The light beam Q incident on the light-receiving means 4 contains information about the amount of light reflected from various parts of the magnetic tape 2, which was luster-scanned by the light beam Q. More specifically, when the light beam Q is incident on the tape area, the amount of light received by the light-receiving means 4 is maximum. When the light beam Q is deviated from the tape area, the amount of received light is zero. If there are tape defects such as scars and scratches in the tape area, the amount of light reflected from the defective part of the tape and incident on the light-receiving means 4 is reduced. Therefore, a check as to whether there are tape defects such as scars and scratches can be obtained by measuring the amount of light received by the light-receiving means 4. Actually, however, the light beam Q is photoelectrically converted by the light-receiving means 4 into a light amount signal, and thus a check as to whether there are any tape defects is done by measuring the light amount signal provided from the light-receiving means 4. FIG. 3(a) shows an example of the waveform of the light amount signal when the tape has a scar or scratch 10 formed in a central portion of the tape width and extending in the longitudinal direction of the tape as shown in FIG. 2. This waveform is at a minimum when the amount of light received by the light-receiving means 4 is at a maximum and at a maximum when the amount of light received is at a minimum.

When the spot of the light beam Q crosses the tape edge, the level of the light amount signal is changed from maximum to minimum or from minimum to maximum. The quickly changing part of the light amount signal where it switches from a minimum to a maximum or vice versa is referred to as an edge signal. The light amount signal from the light-receiving means 4 is supplied to the differentiating circuit 5 to generate a light amount differential signal as shown in FIG. 3(b). The signal obtained from differentiating the edge signal noted above is referred to as an edge differential signal. The light differential signal is supplied to the first circuit 6 for comparison to the predetermined reference level, which is actually two levels with opposite signs, one positive and one negative. When the light amount differential signal becomes higher than a positive reference level, a positive level comparator produces a positive output pulse. When the light amount differential signal becomes lower than a negative reference level, a negative level comparator produces a negative output pulse. FIGS. 3(c) and 3(d) show examples of the waveforms put out by the comparators. The first detection circuit 6 counts the comparator output pulses produced during each half cycle of the light beam scanning. If the count of either comparator output pulses is greater than or equal to 2 or equal to 0, the first detection circuit 6 provides a NG signal. If the count is 1, the circuit 6 provides an OK signal as a first detection signal. It is an excellent feature of the present embodiment that even a tape defect in an edge portion of the tape (for instance within 0.5 mm from the tape edge) can be accurately detected. For example, if there is a gentle bend near the edge of the tape, the absolute value of the level of the edge differential signal corresponding to that portion is reduced as shown in FIG. 4(a). This occurs as a result of a reduction in the amount of light received by the light-receiving means 4 because of a deviation of the angle of reflection of the light beam Q incident on the tape at its edges from or in the direction perpendicular to the plane of paper of FIG. 1. In this case, therefore, the count of the pulses put out by the negative level comparator during the half a cycle light beam scanning is 0 as shown in FIG. 4(b), and the first detection circuit 6 provides an NG signal. However, in rare cases when there is a tape defect in the middle portion of the tape width and there is also a gentle bend in a tape edge portion, the count of the output pulses of either comparator during the afore-mentioned half cycle period T may be 1, and in such a case an OK signal is produced. Generally, however, it is very rare that a tape defect in the middle portion and a bend in the tape edge portion noted above have the same length. In addition, the width of the tape is scanned at close intervals along the tape length. Therefore, the count of either of the level comparator pulses during the half cycle period of the light beam scanning is a value other than 1 (i.e., equal to 0 or greater than or equal to 2), so that is possible to check whether there is a tape defect.

The light differential signal is further supplied to the second detection circuit 7. In this circuit, like in the first detection circuit 6, the level of the light amount differential signal is compared to the predetermined reference level, so that negative level comparator output pulses are produced (FIG. 5(a)). At the same time, positive level comparator output pulses are also produced (FIG. 5(b)). The second detection circuit 7 determines the period S from the rising edge of an output pulse from a negative level comparator circuit till the rising edge of an output pulse from an immediately succeeding positive level comparator circuit by counting the pulses of a clock signal (FIG. 5(c)) during this period. The period S thus obtained is compared to a predetermined reference period. If the two periods are different, an NG signal is produced. If the two periods are equal, an OK signal is produced. In other words, the second detection circuit 7 checks whether the time during which the light differential signal stays within a certain level range, which range is determined by the comparator circuits, matches the predetermined time which results in the absence of any tape defect. When a tape defect is detected by the second detection circuit, it is due to a sharp bend of or damage to a tape edge portion or a deviation from the regular tape width stemming from defective tape cutting.

When tape defects such as scars or scratches are present in the middle portion of the tape width, a positive level comparator output pulse is produced, and the period S is further reduced, so that an NG signal results.

FIG. 6 shows an example of the timing chart for explaining the operation of various parts of the tape defect detector. The abscissa of this timing chart is set such that 0° is taken as a point of mechanical origin when the system described above begins to perform a single checking operation, i.e., a checking of continuously flowing articles, at a constant frequency and also 360° or 0° is taken as an instant when a sequence of handling of the articles, tape drive operation, checking and provision of detection signals are all ended. In this example, a motor for driving the reel 1a, the spool reel, is started at a phase of 142° and stopped 100 msec after passing a phase of 320°. Further, a motor for driving the reel 1b, the tape reel, is started at a phase of 142° and stopped at a phase of 320°. Further, a check gate signal, which is generated by a check gate circuit (not shown) according to the signal from the fiber sensor 8, turns "on" (i.e., equals "1") 465 msec after the passage of a phase of 142° and turns "off" (i.e., equals "0") 100 msec, after the passage of a phase of 320°. The detection of tape defects is performed between the phases of 191° and 335°, and a detection signal indicating the presence of a tape defect is provided between the phases of 334° and 335°.

Figure 7:
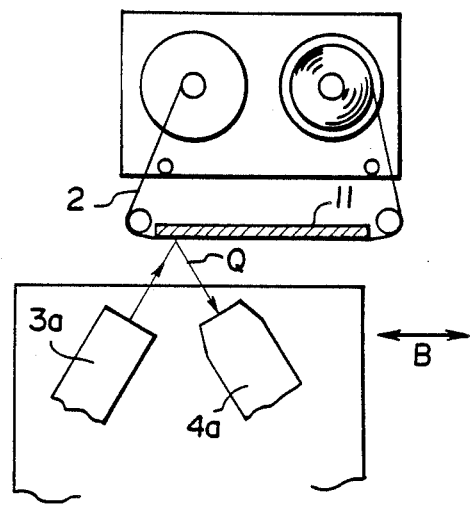
FIG. 7 is a schematic view showing a modification of part of the system shown in FIG. 1.

In the system described above, the light projection means 3 and light-receiving means 4 do not move, and the tape 2 is run past these means. However, it is alternatively possible to hold the tape 2 at a fixed position in space and move light projection means 3a and light-receiving means 4a in unison with each other past the tape in the direction of arrow B by making use of, for instance, a linear slide bearing, as shown in FIG. 7. In this case, a piston-and-cylinder assembly may be used as a means for driving the linear slide bearing. When the tape is held at a fixed position, it is desirable to dispose a flat back plate 11 on the back side of a portion of the tape 2 illuminated by the light beam to place the tape 2 in tension so as to improve the flatness of the tape surface and improve the accuracy of the detection of defects. In this case, it is desirable to make the surface of the back plate 11 an optically dispersing surface by a flattening treatment. When this treatment is provided, light transmitted through the tape 2 or light incident on the back plate 11 near the tape edge can be dispersed by the surface of the back plate 11 to prevent light reflected from the back plate 11 from being incident on the light-receiving means 4a, thus improving the signal-to-noise ratio of the light amount signal.

The light-receiving means 4 and 4a described above may use a one-dimensional image sensor consisting of a CCD or the like. In this case, it is possible to detect tape defects by summing the amount of light received in each individual unit element of the image sensor arranged in a row extending in the direction of the tape width, and from the sum determining the level of the light amount signal and causing the same process as in the above embodiment according to the signal thus obtained.

Further, it is possible to detect tape defects with the above embodiment by having the tape and light-receiving means at fixed positions relative to each other, using a two-dimensional image sensor constituted by a CCD or the like as the light-receiving means, illuminating a wide area of the tape with light from the light projection means all at once to store light amount data for a large tape area in the sensor, and subsequently electrically scanning a large number of elements constituting the sensor.

We claim:

1. A method of detecting defects of a material according to a light amount signal obtained from the surface of said material by scanning the width of the surface of said material with a light beam, said light beam being caused to scan beyond the edges of said material, the light amount signal obtained when said light beam crosses an edge of said material being differentiated to obtain an edge differential signal, a defect of the material in the vicinity of said edge of said material being detected if said edge differential signal has a level different from a predetermined reference level.

2. A method of detecting defects of a material according to a light amount signal obtained from the surface of said material by scanning the width of the surface of said material with a light beam, said light beam being caused to scan beyond the edges of said material, the point in time at which the level of a light amount signal actually changes being compared with the point in time at which the level of the light amount signal changes because said light beam crosses an edge of the material, and detecting a defect of the material when the comparison shows that the two points in time are different.

3. A method according to claim 1, wherein said material is a tape.

4. A method according to claim 2, wherein said material is a tape.

5. A method for detecting defects of a material, said method comprising the steps of:

scanning the width of a surface of said material with a light beam to provide a light amount signal which corresponds to an amount of light reflected from said surface, said light beam scanning beyond edges of said surface of said material;

differentiating said light amount signal to provide a light amount differential signal; and detecting a defect in said material in response to said light amount differential signal.

6. A method according to claim 5, wherein said material is a tape.

7. A method according to claim 5, wherein said material is moved during said scanning step.

8. A method according to claim 5, wherein said material remains in a fixed position during said scanning step.

9. A method according to claim 5, wherein said detecting step comprises the sub-steps of:

providing a positive comparison output pulse each time said light amount differential signal becomes higher than a positive reference level;

providing a negative comparison output pulse each time said light amount differential signal becomes lower than a negative reference level;

determining a first number corresponding to a number of times that said positive comparison output pulse is provided during a predetermined time period;

determining a second number corresponding to a number of times that said negative comparison output pulse is provided during said predetermined time period; and detecting said defect in said material in response to said first number and said second number.

10. A method according to claim 9, wherein said predetermined time period is equal to a half-cycle of the light beam scanning period, and said defect is detected if either of said first and second numbers is equal to zero or is greater than or equal to two.

11. A method according to claim 5, wherein said detecting step comprises the sub-steps of:

providing a negative comparison output pulse each time said light amount differential signal becomes lower than a negative reference level;

providing a positive comparison output pulse each time said light amount differential signal becomes higher than a positive reference level;

determining a period of time between a rising edge of said negative comparison output pulse and a rising edge of said positive comparison output pulse; and detecting said defect in said material in response to said determined period of time.

12. A method according to claim 11, wherein said defect is detected when said determined period of time is not equal to a predetermined period of time.

13. A method according to claim 5, wherein said defect is detected when said light amount differential signal stays within a certain level range for a predetermined period of time.

* * * * *